United States Patent [19]
Imamoto et al.

[11] Patent Number: 5,928,866
[45] Date of Patent: *Jul. 27, 1999

[54] METHOD FOR PREPARING MUTANT GENES

[75] Inventors: Fumio Imamoto, Osaka; Yoshizumi Ishino, Shiga; Mitsuru Furusawa, Tokyo; Hirofumi Doi, Kanagawa, all of Japan

[73] Assignee: Research Development Corporation of Japan, Saitama, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/573,419

[22] Filed: Dec. 15, 1995

[30] Foreign Application Priority Data

Dec. 15, 1994 [JP] Japan .................................... 6-312261
Dec. 15, 1994 [JP] Japan .................................... 6-312262
Jul. 10, 1995 [JP] Japan .................................... 7-173715

[51] Int. Cl.⁶ .................................................... C12Q 1/68
[52] U.S. Cl. .............................. 435/6; 435/440; 435/441; 435/449; 435/448
[58] Field of Search ....................... 435/172.3, 6, 252.33, 435/172.1, 320.1, 440, 441, 449, 448; 935/22, 23, 27, 29, 59, 76, 77, 79

[56] References Cited

PUBLICATIONS

New England BioLabs, 96/97 catalog, p. 208, 1996.
Foster, P.L. In Vivo Mutagenesis, Chapter 5, pp. 114–125. In Methods in Enzymology, Jeffrey H. Miller, ed. Academic Press, Inc., San Diego, 1991.
Gordenin R.A. et al. 1992 Proc. Natl. Acad. Sci USA vol. 89 pp. 3785–3789.
Trinh, TQ. et al. 1991 Science vol. 352, pp. 544–547.
Roberts, J.D. et al. 1993 Biochemistry vol. 32 pp. 483–489.
Vegule, X. et al. 1993 Science vol. 261 pp. 598–600.
Sargentini, N.J. et. al. 1985 Mutation Research 154 pp. 1–27.
Schaaper, R.M. et al. 1989 EMBO Journal vol. 8(11) pp. 3511–3516.
Schaaper, R.M. 1993 J. Biol. Chem vol. 268(32) pp. 23762–23765.
Ciesla, Z. et al 1990 Mol. Gen Genet. vol. 221 (1) pp. 251–255.
Rosenthal, N. 1987 Methods in Enzymology pp. 704–720.
Melchior et al., "Replication–linked strand–specific mutagenesis", Proc. Annu. Meet. Am. Assoc. Cancer Res. 33: A1050, 1992.
Armstrong et al., "Excision repair and gene prientation modulate the strand specificity of UV mutagenesis in a plasmid–borne yeast tRNA gene", Environment. Mol. Mutagen., 25: 12–22, 1995.
Foster et al., "Interactions between epsilon, the proofreading subunit of DNA polymerase III, and proteins involved in the SOS response of *Escherichia coli*", Mol. Gen. Genet. 214:467–473, 1988.

*Primary Examiner*—James Ketter
*Assistant Examiner*—Irem Yucel
*Attorney, Agent, or Firm*—Wenderoth, Lind & Ponack, L.L.P.

[57] ABSTRACT

This invention provides A method for preparing mutant genes, which comprises the steps of constructing a recombinant plasmid DNA by inserting a gene fragment into a plasmid DNA having a unidirectional origin, introducing the recombinant plasmid DNA into host cell lacking DNA error-correcting function to transform the host cell, and culturing the transformant cell in a condition that any mutations of the inserted gene is detectable. According to the present invention, diverse mutant genes can be prepared in a short period of time.

3 Claims, 6 Drawing Sheets

METHOD FOR PREPARING MUTANT GENES

BACKGROUND OF THE INVENTION

1. Field of the Invention

The present invention relates to a method for preparing mutant genes. More particularly, the present invention relates to a method for artificially and efficiently preparing unknown and known mutant genes in a short period of time.

2. Description of Related Art

Diverse and various evolution of organisims are brought about by mutation of genes coding structure and functions thereof.

Mechanisms causing mutations studied include an error of base complementarity upon replication of DNA, an error upon repair of damaged DNA, and transposable elements, but there still remain many unclear points. While the known structural changes include base substitution which causes a missense mutation or a nonsense mutation, a frameshift, and a change on chromosome such as deletion, duplication, inversion and translocation, the probability that these mutations spontaneously occur is very low.

For example, the probability of mispairing during one cycle of DNA replication is estimated at about $10^{-10}$ per base pair.

In order to prepare novel biological species or genes, therefore, it is necessary to artificially induce a DNA mutation.

The conventional practice to induce such a mutation has consisted of treating an individual or cells with a physical or chemical mutagen. Representative applicable physical mutagens include ultraviolet rays (UV) mainly causing base substitution, and ionizing radiations (X-rays, $\gamma$-rays, etc.) inducing marked changes on the chromosome level such as deletion and translocation. The common features in these physical mutagens are simplicity, absence of the risk of residue, and possibility of quantitative handling, although the frequency of induced mutations is not very high. Known chemical mutagens include alkylating agents causing base substitution (eg., ethylmethane sulfonate (EMS), N-methyl-N'-nitro-N-nitrosoguanidine (MNNG), and ethylnitrosourea), base analogs (eg., bromodeoxyuridine, and N4 aminocytidine) and intercalators causing a frameshift (such as ICR compounds). These chemical mutagens have a high frequency of induced mutations and are mainly used for inducing mutations of cultured cells. Particularly, alkylating agents such as EMS and MNNG are widely used because of the high frequency of induced mutations, but are defective in chemical stability, and tend to induce multiple mutations. It is therefore considered necessary to be careful in using them.

It is possible to increase the occurring frequency of mutations 100~1000 times by the use of these physical and chemical mutagens. It is however important to appropriately select a kind of mutagen according to the target mutation, and at the same time, to set an appropriate concentration of mutagen, treatment time, mutation expressing time and number of plates of propagated cells. The variables must further be set after repeated trials and errors for each cell covered.

For *Escherichia coli* and yeasts, on the other hand, methods for artificially preparing mutant strains by the use of gene manipulation are known, including, for example, a site-specific mutation using M13 phage for *Escherichia coli*, introduction of transposon using a suicide vector, and gene destruction using an insertional vector for yeasts. For *Escherichia coli*, there are also known a mutant strain (mut) which increases the mutation rate per generation, and a mutant strain (recA$^-$, umuC$^-$) which causes almost no mutation on the contrary.

SUMMARY OF THE INVENTION

The present invention has an object to provide a novel method which permits preparation of a new mutant gene sequence simply in a short period of time by inducing base substituting mutation upon replication of DNA at such a high frequency as $5 \times 10^{-3}$ without using a physical or chemical mutagen.

The present invention provides a method for preparing mutant genes, which comprises constructing a recombinant plasmid DNA by inserting a gene fragment into a plasmid DNA having a unidirectional origin, introducing the recombinant plasmid DNA into host cell lacking DNA error-correcting function to transform the host cell, and culturing the transformant cell in a condition that any mutations of the inserted gene is detectable.

The present invention provides also an embodiment wherein the gene fragment is inserted into the plasmid DNA in the orientation that the direction of the gene's transcription is the same as that of the plasmid DNA's replication from the origin thereof.

The present invention provides another embodiment wherein the gene fragment is inserted into a cleaved portion of the plasmid DNA where is downstream and within 2,500 bp from the origin thereof.

The present invention provides further another embodiment wherein the host cell is *Escherichia coli* KH1379 (dnaQ 49, recA$^+$) strain.

The present invention provides further another embodiment wherein the transformant cell is cultured in a stressful condition, and a mutant gene tolerant to the condition is detected.

The method and the embodiments presented above permit efficient preparation of diverse mutant genes in a short period of time.

DETAILED DESCRIPTION OF THE INVENTION

Figure 1:
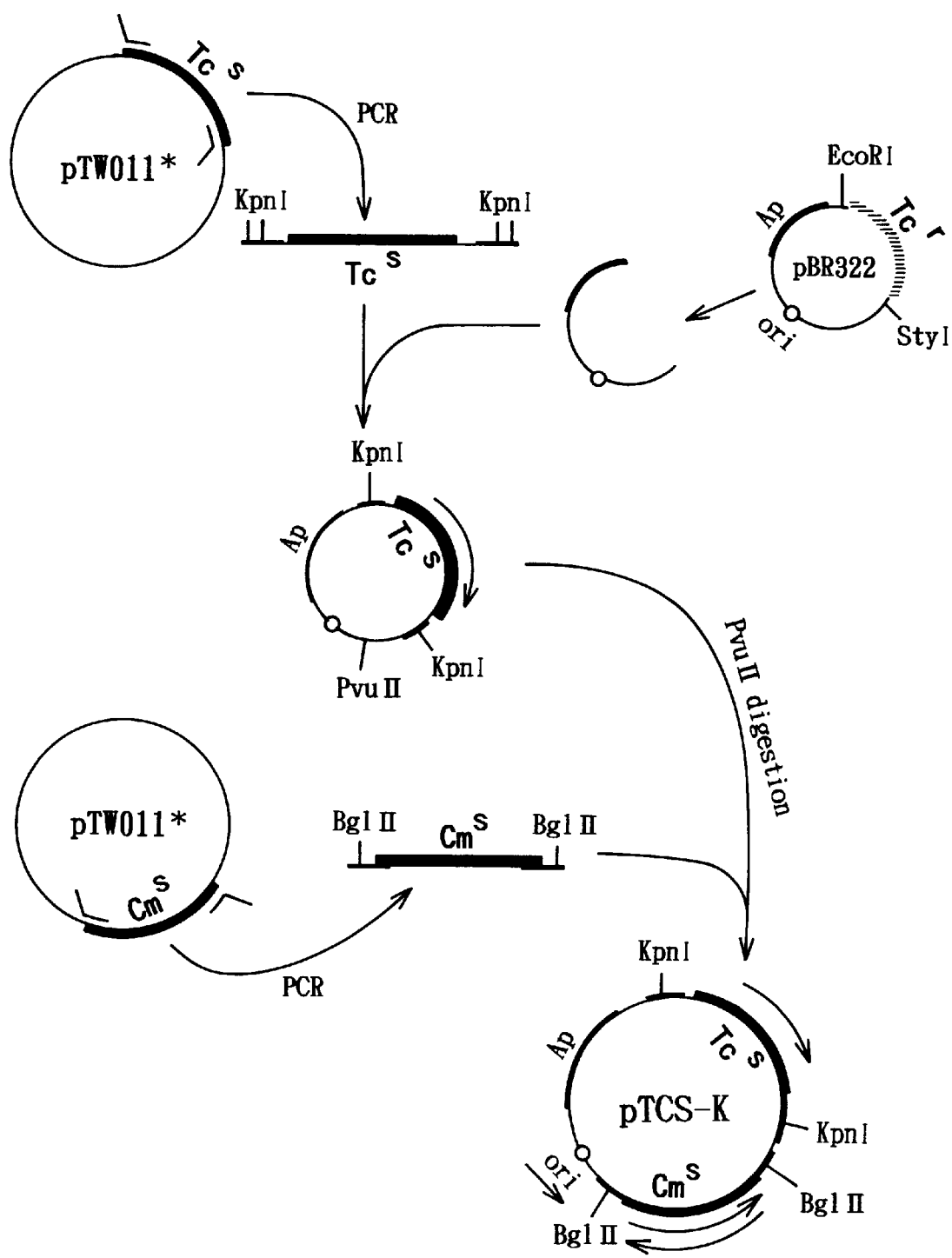
FIG. 1 is a schematic view illustrating a preparing process of recombinant plasmid DNA described in Example 2.

In the method for preparing mutant genes of the present invention, the first step comprises constructing a recombinant plasmid DNA by inserting a gene fragment into a plasmid DNA having a unidirectional origin. The gene fragment is a DNA fragment containing a gene sequence to achieve induction of mutation, and the gene sequence can cover a genomic DNA or cDNA which codes structural genes of all organisms. The plasmid DNA having a unidirectional origin is a circular double-stranded plasmid DNA which causes division and replication from a single origin in a single direction. A preferable example of such a plasmid DNA is a plasmid having a unidirectional origin ColE1 of plasmid pBR322.

In this first step, furthermore, a preferable embodiment is to insert the gene fragment into the plasmid DNA so that the fragment is transcribed in the same direction as that of replication from the origin. More specifically, this direction of gene fragment insertion means that the gene fragment is inserted so that a promotor sequence and/or enhancer sequence controlling transcription and expression of the gene sequence is positioned, and then the gene sequence is located in the downstream of this control sequence along the direction of division and replication from the unidirectional origin. As is clear from examples presented later, insertion of the gene fragment in this direction permits promotion of the occurring frequency of mutation of the inserted gene sequence. This may be because that by inserting the gene fragment in the direction as this embodiment the transcription template of the gene is positioned on the lagging daughter strand, and mutation rate of this lagging strand is 10~100 times higher than that of leading strands at each replication of the gene fragment.

Another embodiment in this first step is to insert the gene fragment into a cleaved portion of the plasmid DNA within 2,500 bp from the origin in the downstream thereof. More specifically, this embodiment method is based on a novel fact that an insertion position of the gene fragment closer to the origin leads to an increased occurring frequency of mutations, and an insertion position apart by more than 2,500 bp results in a decreased occurring frequency of mutations. The gene fragment for inducing mutation should preferably be inserted at a portion near the origin in the downstream thereof, and a marker gene used for selecting transformant cells in a subsequent step should preferably be inserted at a position far from the origin to construct a recombinant plasmid. The effect of insertion position of the gene fragment will more clearly be described in examples presented later.

This insertion of the gene fragment into the plasmid DNA in the first step may be accomplished in accordance with a known method using, for example, a restriction enzyme or ligase.

The second step in the method of the present invention comprises preparing a transformant cell by introducing the recombinant plasmid DNA into the host cell lacking DNA error-correcting function. An example of such a host cell lacking the DNA error-correcting function is, for example, *Escherichia coli* dnaQ mutant strain. A preferable example of *Escherichia coli* dnaQ mutant strain is *Escherichia coli* KH1379 (dnaQ 49, recA$^+$) which is a temperature-sensitive mutant strain relative to mutation induction. Because this *Escherichia coli* dnaQ 49 strain has a mutation in the gene coding DNA polymerase III ε factor and inactivates the factor at high temperature (37° C.), it is impossible to correct a base substituting mutation upon DNA replication. In various organisms under natural condition, the probability of occurrence of base substituting mutation during a single run of DNA replication is estimated to be about $10^{-10}$ per base pair. In this KH1379 dnaQ 49 strain, however, the defect of DNA polymerase III ε factor increases the probability from $10^3$ to $10^5$ times as high, thus permitting accumulation of diverse and various mutations. This mutation rate of KH1379 dnaQ 49 strain is more than twice as much as that of XL1Red strain having mutations in DNA error-correcting functions S, T and D which is a well known mutations-inducing *Escherichia coli* strain (Atrategies, 7, 32, 1994).

Introduction of the recombinant plasmid DNA into the host cell may be accomplished by approximately selecting one from such conventional methods as the calcium method, the protoplast method, the calcium phosphate precipitation method, and the liposome method, depending upon the kind of a particular host cell. When the host cell is *Escherichia coli*, for example, the recombinant plasmid DNA can be introduced by the application of the calcium chloride method or the like. A transformant cell can be selected in accordance with a conventional method with a selection marker (a drug resistance gene, etc.) incorporated into the recombinant plasmid DNA.

The third step in the present invention comprises culturing the above-mentioned transformant cell under conditions capable of detecting mutation of inserted gene. When detecting a new mutant gene which expresses a known protein, for example, the transformant cell is cultured in the presence of an indicator (an antibody against the protein, for example) which detects expression of this known protein. Or, when detecting a gene resistant to various stress factors (drugs, chemicals, metals, heat, radiation, etc.), the transformant cell may be cultured in the presence of these stress factors. It is possible to detect a target mutant gene from a viable colony in the presence of stress factors. Furthermore, by culturing the transformant cell in a usual way to accumulate mutations of inserted genes, then isolating recombinant plasmid DNA, and introducing this isolated plasmid DNA into another host cell (a cell having the DNA error-correcting function, for example, *Escherichia coli* recA$^-$ strain), this second transformant cell may be cultured under conditions permitting detection of mutations. In this method, it is possible to produce a gene having a desired character in a condition no more causing mutation of genes after providing variations of mutant genes through culture in a host cell lacking DNA error-correcting function.

Now, the method for preparing mutant genes of the present invention will be described in further detail by means of examples. The present invention is not limited to the examples shown below.

EXAMPLE 1

A DNA sequence containing ampicillin resistance gene (Amp$^R$) was cloned to plasmid DNA having a ColE1 type origin of plasmid pBR322 to prepare recombinant plasmid pTC2 (Amp$^R$).

This pTC2 (Amp$^R$) was introduced into *Escherichia coli* KH1379 strain, and after screening the transformant with ampicillin resistance, and logarithmic phase growth (30 cycles per day; for four days) of the transformant was continuously caused while inducing dnaQ 49 mutation at a temperature of 37° C., thus replicating pTC2 (Amp$^R$).

Then, this pTC2 (Amp$^R$) was isolated from the *Escherichia coli* KH1379 strain, introduced into *Escherichia coli* JM109 strain which was rccA$^-$ strain to culture the transformant on a medium containing cefotaxime and the transformant having formed a colony on a medium having a ten-times concentration (×10 Cef) of cefotaxime MIC (0.02 μg/ml) was screened.

As a result, cefotaxime resistant cells (×10 Cef) were derived at a high frequency as $1.2 \times 10^{-1}$ (12%) relative to ampicillin resistant cells (approx. 130 colonies) from the *Escherichia coli* transformed by the recombinant pTC2

(Amp$^R$) replicated for four days in *Escherichia coli* KH1379 strain. Plasmid was further separated from this cefotaxime-resistant cells and introduced again into *Escherichia coli* JM109 strain. The resultant transformant cells similarly exhibited cefotaxime resistance. In the case of pTC2 (Amp$^R$) not subjected to mutation, no cefotaxime-resistant cells were emerged from ampicillin-resistant cells in such large quantity as from $6 \times 10^3$ to $2 \times 10^5$ colonies.

According to the method of the present invention, therefore, it was confirmed that pTC2 (Amp$^R$) containing Amp$^R$ gene has acquired cefotaxime resistance (Cef$^R$) at a high probability, in spite of the mutation manipulation for a short period of time of only four days.

EXAMPLE 2

Recombinant plasmid pTCS-K having a plasmid pBR322 ColE1 type origin and two kinds of drug-sensitive gene (chloramphenicol-sensitive gene: Cm$^S$ and tetracycline-sensitive gene: Tc$^S$) was prepared in accordance with a process shown in FIG. 1. This recombinant pTCS-K is composed of a 1334 bp DNA fragment containing Cm$^S$ cut off from pTWS011 and 1375 bp fragment containing Tc$^S$, bonded to a fragment (2992 bp) containing pBR322 ampicillin-resistance gene (Ap$^R$) and an origin (ori).

Figure 2:
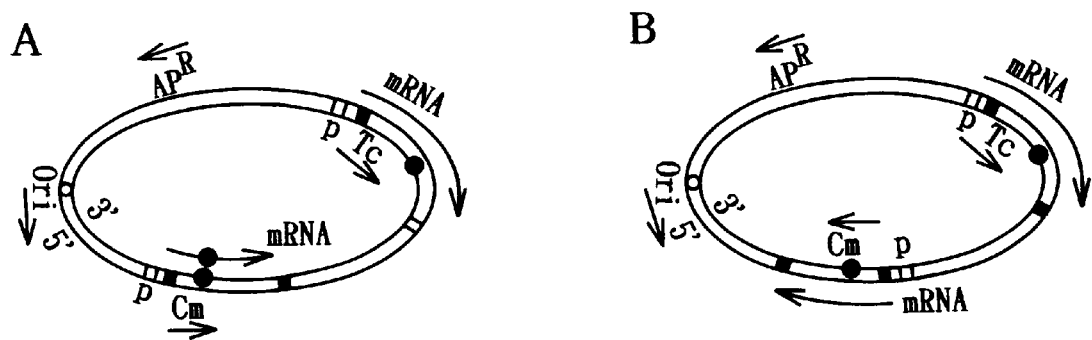
FIG. 2A is a structural diagram of recombinant plasmid pTCS-K19 series.
FIG. 2B is a structural diagram of recombinant plasmid pTCS-K20 series of Example 2.

For the fragment containing Cm$^S$, a pTCS-K19 series (K-19, K-2, K-47, K-31) shown in FIG. 2(A) and a pTCS-K20 series (K-20, K-1, K-44, K-34) shown in FIG. 2(B) were prepared by changing the direction of insertion. More specifically, for the pTCS-K19 series, Cm$^S$ was transcribed in the same direction as that of division and replication of plasmid DNA, and for the pTCS-K20 series, on the other hand, Cm$^S$ was transcribed in the reverse direction to that of division and replication of plasmid DNA. In the both cases, Tc$^S$ was transcribed in the reverse direction to that of division and replication of plasmid DNA.

The thus prepared pTCS-K was introduced into *Escherichia coli* KH1379 (dnaQ 49) strain, and cultured in an LB medium containing ampicillin at 24° C. for 16 hours. Mutation of dnaQ 49 was then induced by further culturing the thus cultured pTCS-K at 37° C. for 16 hours.

After the above-mentioned culture at the individual temperatures, the number of surviving cells in the LB medium containing ampicillin alone or ampicillin and chloramphenicol was counted to calculate the Cm$^S$→Cm$^R$ mutation rate in the form of a ratio of ampicillin-resistant cells to chloramphenicol-resistant ones.

The results are as shown in Table 1: these results permit confirmation that mutations from sensitivity (Cm$^S$) into resistance to chloramphenicol (Cm$^R$) in transformation by the pTCS-K19 series are about ten time more than those in transformation by the pTSC-K20 series. The difference in the mutation rate between the pTCS-K19 series and the pTCS-K20 series was more clearly known by inducing mutation of dnaQ 49 (cultured at 37° C.)

TABLE 1

| Plasmids | Direction of replication & expression | | Mutation rate to Cm$^R$ (×10$^{-6}$) | |
|---|---|---|---|---|
| | Ori | Cm$^S$ | 24° C. | 37° C. |
| pCTS-K20 | | | 3 | 94 |
| pCTS-K1 | → | ← | 8 | 60 |
| pCTS-K44 | | | 7 | 110 |
| pCTS-K34 | | | 8 | 83 |
| pCTS-K19 | | | 45 | 1100 |

TABLE 1-continued

| Plasmids | Direction of replication & expression | | Mutation rate to Cm$^R$ (×10$^{-6}$) | |
|---|---|---|---|---|
| pCTS-K2 | → | → | 55 | 1200 |
| pCTS-K47 | | | 21 | 1300 |
| pCTS-K31 | | | 37 | 800 |

Then, KH1379 transformed through introduction of pTCS-K19 and pTCS-K20, respectively, was cultured in an LB medium containing ampicillin at 24° C. for five hours, and after changing the culture conditions to 37° C., mutation of dnaQ 49 was induced to measure mutant cells to Cm$^R$. This measurement was accomplished by measuring absorbance of OD650 every hour from thermal induction in an LB medium containing chloramphenicol and ampicillin.

The results are as shown in Table 2: the difference in the mutation rate for transformed cells between pTCS-K19 and pTCS-K20 is larger according as the thermal mutation induction time increases even to eight times as large after the lapse of six hours.

TABLE 2

| Culturing hours at 37° C. | OD$_{550}$ | | Mutation rate to Cm$^R$ (×10$^{-6}$) | | |
|---|---|---|---|---|---|
| | K19 | K20 | K19 | K20 | K19/K20 |
| 0 | 0.34 | 0.33 | | | |
| 1.0 | 1.70 | 1.68 | 40.0 ± 13.6 | 18.9 ± 4.4 | 2.1 |
| 2.0 | 2.70 | 2.65 | 118.3 ± 57.0 | 44.7 ± 5.2 | 2.6 |
| 3.0 | 3.90 | 4.00 | 249.1 ± 23.5 | 77.8 ± 60.2 | 3.6 |
| 4.0 | 4.60 | 4.50 | 271.1 ± 16.8 | 80.0 ± 44.0 | 3.4 |
| 5.0 | 5.20 | 5.30 | 256.5 ± 92.1 | 40.6 ± 29.8 | 6.3 |
| 6.0 | 5.60 | 5.50 | 174.1 ± 29.5 | 21.6 ± 1.3 | 8.1 |
| 7.5 | 6.90 | 6.70 | 70.7 ± 8.4 | 8.3 ± 2.4 | 8.5 |
| 9.5 | 7.20 | 7.20 | 67.1 ± 2.6 | 8.1 ± 0.3 | 8.3 |

As is confirmed from these results, mutation of gene sequence occurs at a rate far higher in the recombinant plasmid DNA for which genes are transcribed in the same direction as that of division and replication than the recombinant plasmid DNA for which inserted genes are transcribed in the reverse direction to that of division and replication of plasmid DNA.

EXAMPLE 3

Figure 3:
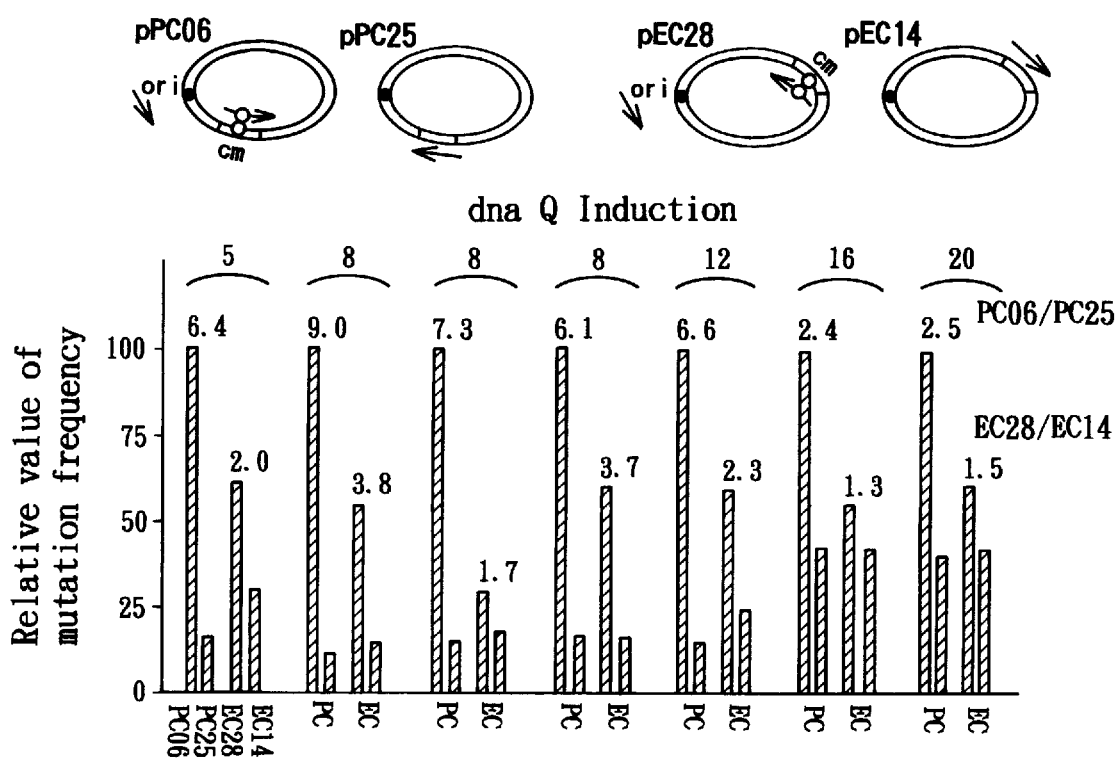
FIG. 3 shows structural diagrams of recombinant plasmid DNAs prepared in Example 3 and a histogram illustrating the ratios of mutation rates of *Escherichia coli* available by introducing the plasmids.

Four kinds of recombinant plasmid, the configurations of which are as shown in the upper portion of FIG. 3, were prepared by bonding a gene fragment containing a chloramphenicol-sensitive gene (Cm$^S$) to a DNA fragment containing a ColE1 type origin (ori) of plasmid pBR322. More specifically, genes Cm$^S$ are bonded at a position 830 bp apart from the origin in pPC06 and pPC25 but in opposite directions; pPC06 transcribes mRNA of Cm$^S$ in the same direction as that of division and replication, and pPC25 transcribes Cm$^S$ in the reverse direction. In pEC28 and pEC14, on the other hand, the genes Cm$^S$ are bonded at a distance of 2700 bp from the origin and Cm$^S$ transcribing directions are reverse to each other.

The mutation rate from sensitivity (Cm$^S$) to resistance (Cm$^R$) to chloramphenicol was calculated by introducing the thus prepared recombinant plasmid into *Escherichia coli* KH1379 (dnaQ 49), culturing the transformant in an LB medium containing chloramphenicol at 37° C. for 20 hours, and counting the number of surviving cells at an arbitrary time point.

The results are as shown in the lower portion of FIG. 3. As is clear from this graph, the results permit confirmation that the mutation rate from sensitivity ($Cm^S$) to resistance ($Cm^R$) to chloramphenicol is larger in transformation accomplished through introduction of pPC06 or pEC28 for transcribing inserted genes in the same direction as that of division and replication than in introduction of pPC25 or pEC14 having genes in the reverse direction. This confirms again that inserting a gene so as to cause transcription in the same direction as that of division and replication leads to a higher mutation rate.

However, as compared with pEC28/14 in which the inserted gene $Cm^S$ is more distant from the origin, pPC06/25 having the gene closer to the origin results in a more extreme ratio of mutation rates between different directions of gene transcription. This suggests that, when inducing many mutation sequences from inserted genes, it suffices to insert a gene at a position close to the origin.

Figure 4:
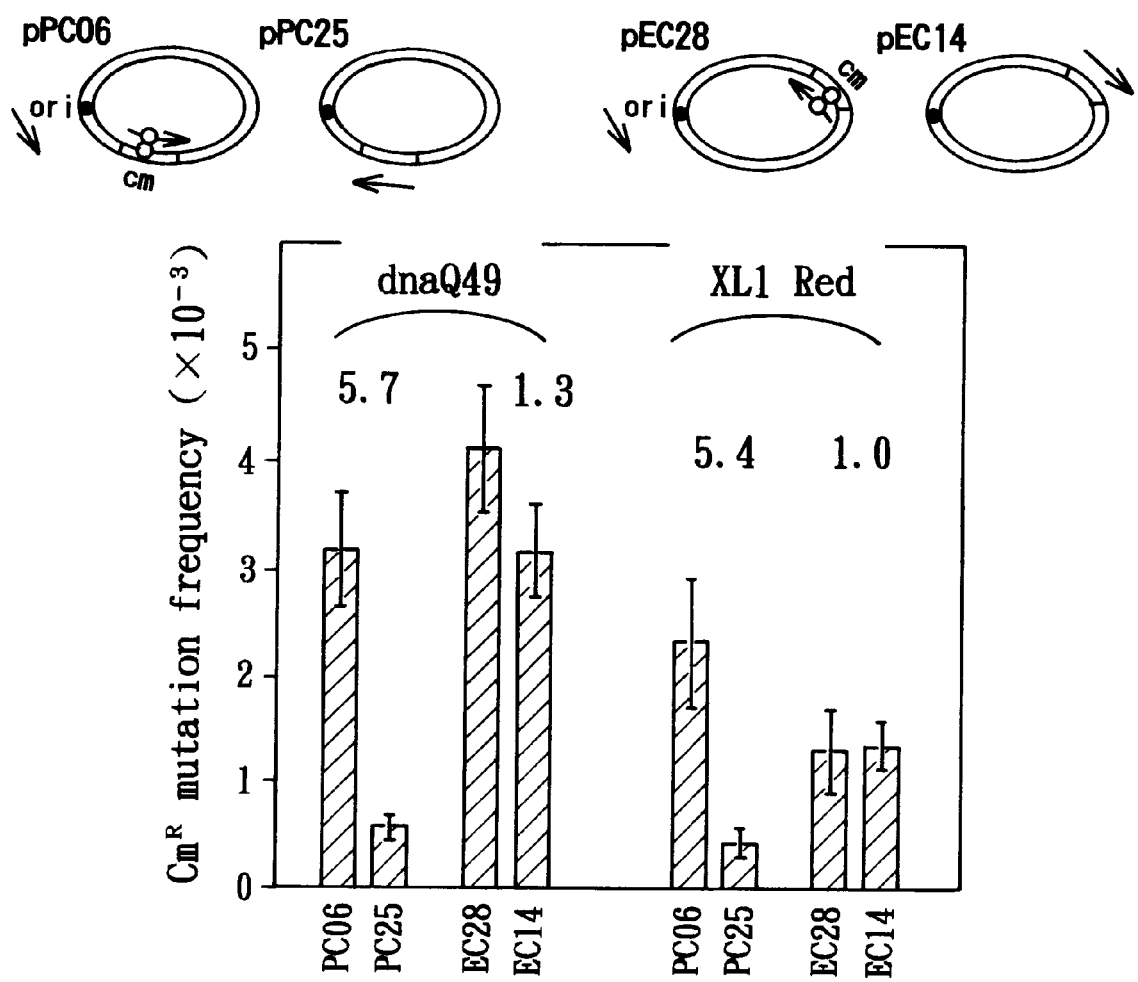
FIG. 4 shows structural diagrams of recombinant plasmid DNAs prepared in Example 3 and a histogram illustrating the ratios of mutation rates of two kinds of *Escherichia coli* available by introducing the plasmids.

Such a positional effect of inserted gene was confirmed not only for dnaQ 49 strain, but also in cases where *Escherichia coli* XL1Red strain having mutation in mismatch-correcting factors S, T and D served as a host (see FIG. 4).

Figure 5:
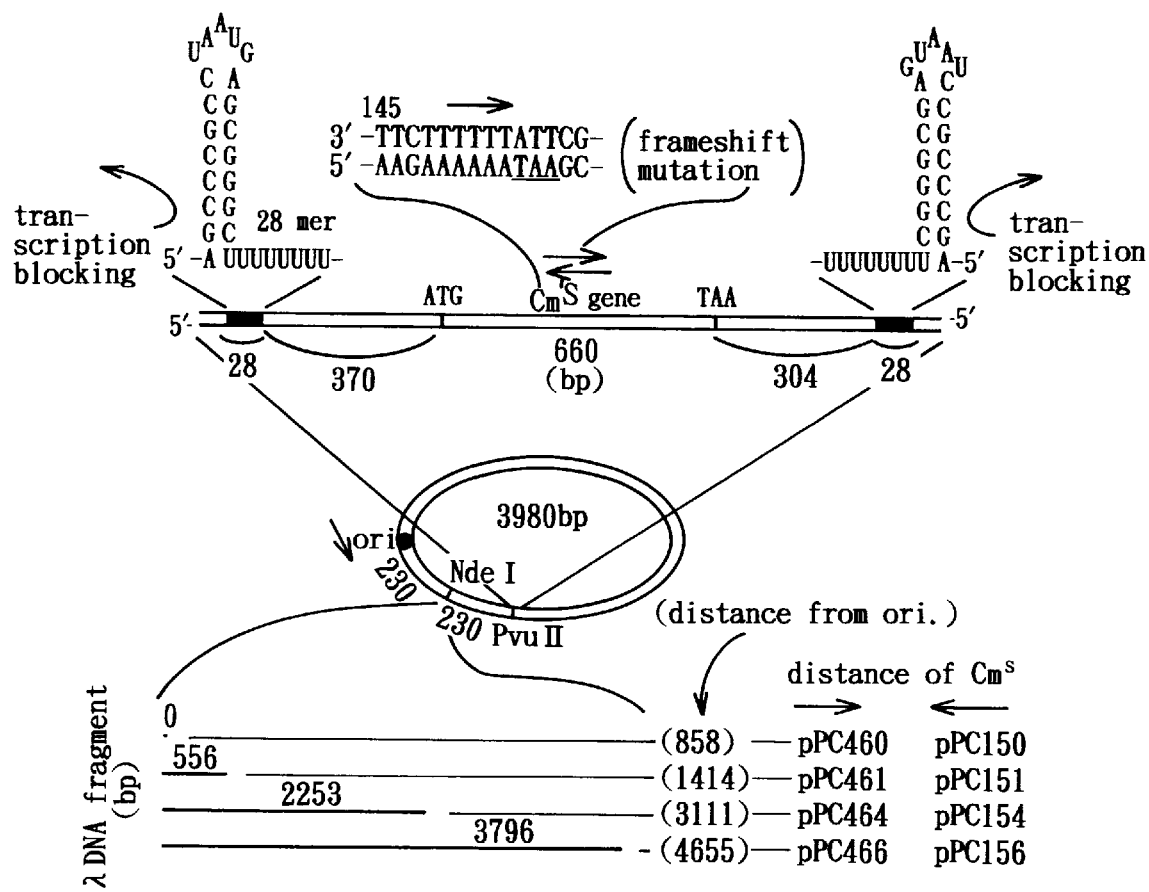
FIG. 5 shows structural diagrams of another recombinant plasmid DNA prepared in Example 3, and a structural diagram of a DNA fragment connected to the plasmid DNA.

Then, the distance between the origin and the inserted gene and the difference in mutation rate were studied. For this purpose, a recombinant plasmid pPC series having a configuration as shown in FIG. 5 was prepared. This pPC series was prepared by connecting DNA fragment having a total length of 1642 bp and containing 660 bp $Cm^S$ gene was connected at a position of 460 bp in the downstream of the origin (ori) in a different direction. To prevent read-through transcription from the plasmid DNA sequence for connection, a strong transcription-terminating sequence derived from triptophan operon (trpa) of *Escherichia coli* were connected to the both sides of the DNA fragment. The base sequence shown for the $Cm^S$ gene suggests that a frameshift is produced as a result of insertion of T-A pair shown with thick characters in this sequence into the sequence of the resistance gene $Cm^R$, and underscored TAA (termination codon) prevents transcription and expression of the gene, thereby the gene being to sensitive to chloramphenicol ($Cm^S$). If this T-A pair is eliminated by point mutation, therefore, this $Cm^S$ gene can return to $Cm^R$.

The distance between the origin and the $Cm^S$ gene was adjusted by inserting λ DNA fragment having a different length at a position of 230 bp from the origin in the pPC series.

Eight kinds of recombinant plasmid DNA as shown to the right in the lower portion of FIG. 5 were prepared with different distances and different directions of $Cm^S$ genes.

These plasmid DNA were introduced into *Escherichia coli* KH1379 (dnaQ 49) strains, and cultured at 37° C. for eight hours or for 13 hours to induce mutation, and the mutation rate from $Cm^S$ to $Cm^R$ was determined with the number of surviving transformants into which plasmid DNA were introduced as the indicator.

Figure 6:
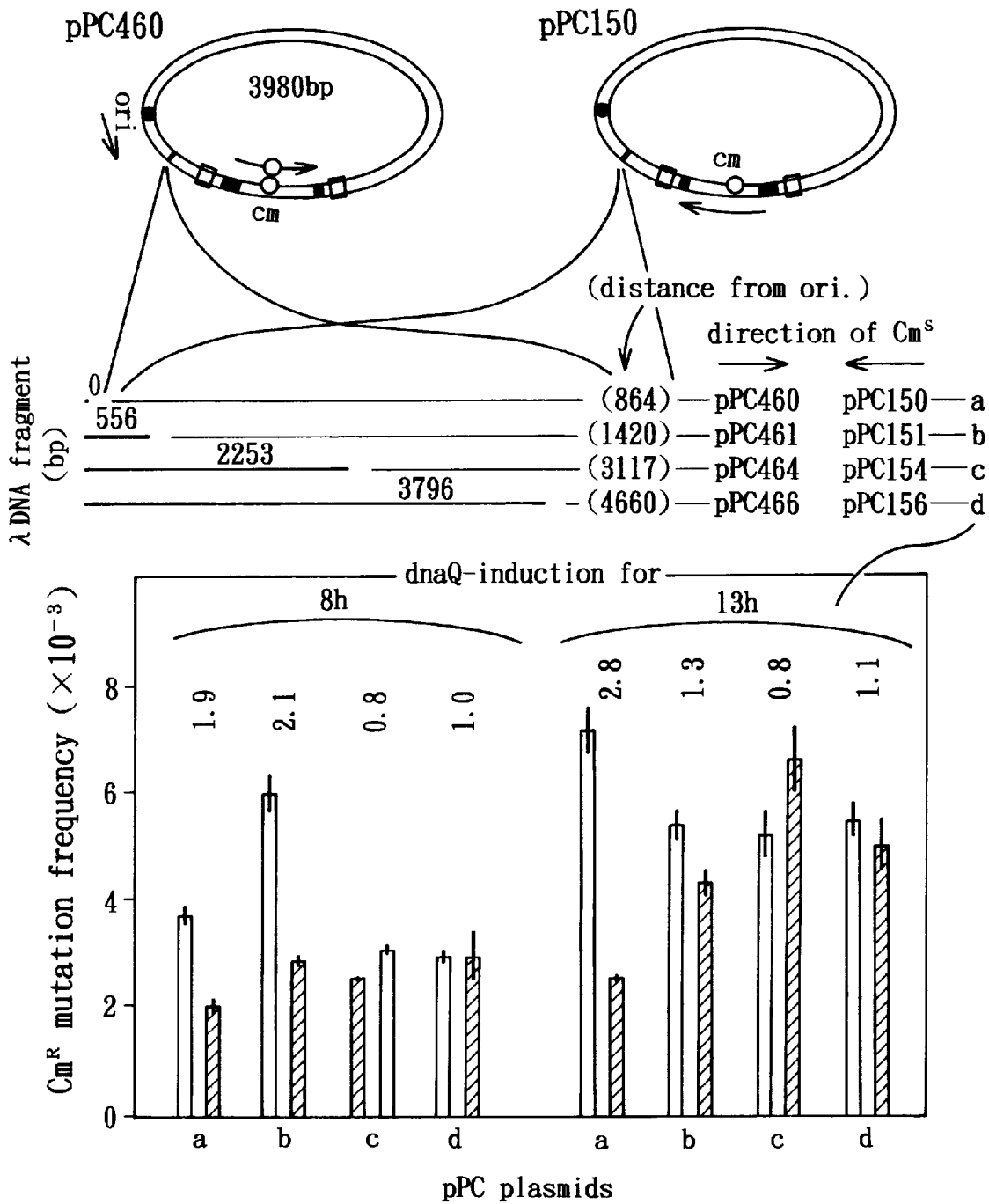
FIG. 6 is a histogram illustrating the ratios of mutation rates of *Escherichia coli* prepared by introducing the recombinant plasmid DNA shown in FIG. 5.

The results are as shown in the graph in the lower part of FIG. 6. More specifically, as compared with the host having introduced pPC150 and pPC151 connected with $Cm^S$ gene of a low mutation rate at positions of 864 bp and 1420 bp from the origin, respectively, the host having introduced pPC460 and pPC461 having $Cm^S$ gene at these positions, respectively, showed a number of mutant about twice as large in culture for eight hours and from 1.3 to 2.8 times as large even in culture for 13 hours. In the case of $Cm^S$ gene of 3116 bp (pPC464/154) and 4654 bp (pPC466/156) from the origin, in contrast, almost no difference in mutation rate was observed between different directions of insertion of the gene. These results permit confirmation that, when inducing many mutations of exogenous genes, it suffices to use a position of connection of a distance in the downstream of the origin of up to 2500 bp, or more preferably, of up to 1500 bp. It is also clear, on the other hand, that the difference in mutation rate caused by the difference in the connecting direction of gene can be reduced by connecting the inserted gene to a position of over 2500 bp from the origin.

What is claimed is:

1. A method for preparing mutant genes, which comprises the steps of:

constructing a recombinant plasmid DNA by inserting a gene into a plasmid DNA having a unidirectional origin, wherein the gene is inserted into the plasmid DNA in an orientation such that the direction of the gene's transcription is the same as that of the plasmid DNA's replication from said origin, and wherein the gene is inserted into the plasmid DNA within 1,500 bp from the 3'-end of said origin, introducing the recombinant plasmid DNA into a host cell lacking a DNA error-correcting function to transform the host cell, and culturing the transformant cell under conditions such that any mutations of the inserted gene are detectable.

2. The method according to claim 1, wherein the host cell is *Escherichia coli* KH1379 (dnaQ 49, $recA^+$) strain.

3. The method according to claim 1, wherein the transformant cell is cultured in a stressful condition, and a cell tolerant to the condition is detected.

* * * * *

UNITED STATES PATENT AND TRADEMARK OFFICE
CERTIFICATE OF CORRECTION

PATENT NO. : 5,928,866
DATED : July 27, 1999
INVENTOR(S) : Fumio Imamoto et al.

Page 1 of 1

It is certified that error appears in the above-identified patent and that said Letters Patent is hereby corrected as shown below:

Title page,
Item [73], please insert the following second Assignee: -- TAKARA SHUZO CO., LTD. KYOTO, JAPAN --

Signed and Sealed this

Seventh Day of August, 2001

*Attest:*

*Attesting Officer*

NICHOLAS P. GODICI
*Acting Director of the United States Patent and Trademark Office*